United States Patent [19] [11] 4,197,415
Hideyuki et al. [45] Apr. 8, 1980

[54] PROCESS FOR PREPARING CYCLIC OLEFINS BY SELECTIVE PARTIAL HYDROGENATION OF AROMATIC HYDROCARBONS

[75] Inventors: Aizawa Hideyuki, Aichi; Kuroda Akio, Kawasaki, both of Japan

[73] Assignee: Toray Industries, Inc., Tokyo, Japan

[21] Appl. No.: 5,868

[22] Filed: Jan. 23, 1978

Related U.S. Application Data

[63] Continuation of Ser. No. 837,311, Sep. 28, 1977, abandoned.

[30] Foreign Application Priority Data

Oct. 8, 1976 [JP] Japan ................................. 51-120422
Nov. 26, 1976 [JP] Japan ................................. 51-141107

[51] Int. Cl.$^2$ ......................... C07C 5/02; C07C 13/20
[52] U.S. Cl. ..................................... 585/23; 585/269; 585/277
[58] Field of Search ............. 260/667, 666 A; 585/23, 585/269, 277

[56] References Cited

U.S. PATENT DOCUMENTS

| 2,238,594 | 4/1941 | Malisher | 585/266 |
| 3,140,322 | 7/1964 | Frilette et al. | 858/270 |
| 3,183,278 | 5/1965 | Koch | 585/266 |
| 3,227,768 | 1/1966 | Cole et al. | 585/266 |
| 3,755,148 | 8/1973 | Mickelson | 585/277 |
| 3,912,787 | 10/1975 | Nowack et al. | 585/268 |
| 3,925,494 | 12/1975 | Fahey | 585/277 |

Primary Examiner—Veronica O'Keefe
Attorney, Agent, or Firm—Miller & Prestia

[57] ABSTRACT

Aromatic hydrocarbons are selectively partially hydrogenated to cyclic olefins by contacting the aromatic hydrocarbon with hydrogen and a ruthenium catalyst in an aqueous dispersion containing a salt of a phosphorus acid.

21 Claims, No Drawings

PROCESS FOR PREPARING CYCLIC OLEFINS BY SELECTIVE PARTIAL HYDROGENATION OF AROMATIC HYDROCARBONS

This is a continuation, filed Sept. 28, 1977 now abandoned.

BRIEF SUMMARY OF THE INVENTION

This invention relates to the hydrogenation of aromatics. More specifically it relates to a process for preparing a cyclic olefin by selective partial hydrogenation of aromatic hydrocarbons using a ruthenium catalyst in an aqueous phase.

Cyclic olefins, such as cyclohexene, are useful as a raw material for preparing monomers for synthetic polymers. The cyclic olefins have a relatively high cost because of the difficulty in manufacturing such compounds.

The partial selective hydrogenation of aromatics to cyclic olefins has been considered to be one of the most simple and economical ways to manufacture cyclic olefins such as cyclohexene. In this way, however, there is difficulty in that the cyclic olefin is ready to a be further hydrogenated to cycloalkane, and the selectivity to the cyclic olefin is not high enough. The present invention aids in solving these problems by providing a method to improve the selectivity of the partial hydrogenation.

According to the prior art, there are several known methods to produce cyclic olefins by the selective hydrogenation of aromatic hydrocarbons.

In U.S. Pat. No. 3,912,787 there is disclosed a method for partial hydrogenation using a ruthenium-containing catalyst which is promoted by a metal under an acidic or neutral condition. In this method, however, the selectivity or yield of the cyclic olefin is not high enough to permit practice of this reaction on an industrial scale. Therefore it is necessary to further improve the catalyst system. According to the present invention a higher selectivity can be attained.

In U.S. Pat. No. 3,767,720, a comparatively high selectivity to selective partial hydrogenation has been attained using a reduced cation of a Group VIII metal in an alkaline aqueous phase. The alkaline aqueous phase used in this method is corrosive under usual reaction conditions, and it causes problems in the selection of the reactor material and the contamination of the catalyst system. Therefore this method is not practical for the industrial production of cyclic olefins.

Thus an object of the present invention is to provide an improved method for producing cyclic olefins by the selective partial hydrogenation of aromatics. Another object of the present invention is to provide a simple and improved catalyst system for the selective partial hydrogenation of aromatics.

Other objects and aspects of the present invention will be understood from the following description in the specification and claims.

DETAILED DESCRIPTION OF THE INVENTION

We now have found that the coexistence of a salt of a phosphorus containing acid in an aqueous selective partial hydrogenation system containing a ruthenium catalyst highly improves the selectivity to the cyclic olefin from the corresponding aromatics.

In accordance with the invention, aromatic hydrocarbons are selectively partially hydrogenated to the corresponding cyclic olefin in an improved yield and selectivity.

In the process of the present invention the hydrogenation reaction is effected under a hydrogenation condition with a ruthenium catalyst in an aqueous dispersion containing at least one salt of a phosphorus acid such as the phosphates or phosphites.

The salt of the phosphorus containing acids used in the process of this invention may include orthophosphates, metaphosphates, pyrophosphates polyphosphates, hypophosphates, phosphites and hypophosphites. In these salts, one or more protons of the corresponding phosphorus acids is replaced by a metal ion. For the purpose of the present invention the metal ion may preferably be selected from the metal elements belonging to Groups II to VIII of the periodic table. More preferably, cobalt, nickel, and copper salts may be used. Most of these salts may be unsoluble or slightly soluble in water and aromatic hydrocarbons, and may constitute a slurry, i.e. a dispersion of these salts in water and an aromatic hydrocarbon. In the form of the slurry, the phosphorus acid salt has a sufficient effect to improve the selectivity of the partial hydrogenation.

The amount of the salt added in the reaction mixture is not specifically restricted, but the practical amount is about 0.5 to 2000 part by weight per one part of ruthenium metal contained in the catalyst. When a ruthenium catalyst supported on a carrier is used, there is used about 0.001 to 100, preferably 0.1 to 50 parts by weight per one part of the ruthenium catalyst, inclusive of the carrier. The phosphorus acid salts may be calcined before being added to the reaction mixture. The combined use of more than two kinds of the phosphorus acid salts is also possible.

The mechanism of the improvement by the reaction modifier, and phosphorus acid salts is not completely understood, but it is presently believed that the existence of a phosphorus acid salt is capable of significantly influencing the selectivity of the reaction.

The ruthenium catalyst used in the process of the present invention is not specifically restricted except that it should contain ruthenium metal as a catalyst component. Preferably the ruthenium catalyst may be supported by a carrier, the kind of which considerably affects the catalytic activity and selectivity in the partial hydrogenation. Preferable support carriers include sili -aluminas, and various kinds of zeolite are more preferable. Metal powder and an insoluble phosphorus acid salt which are insoluble in the reaction mixture may also be preferably used as a carrier in some cases.

The ruthenium may be supported on such carriers according to conventional methods such as dipping, ion-exchanging and coprecipitating.

The catalyst supported on the carrier may be activated by being contacted with hydrogen or another reducing agent. In some cases the activation may be carried out in the reaction mixture of the partial hydrogenation reaction.

The ruthenium catalyst may preferably be promoted by being associated with another metal. The promoting component may be selected from the group consisting of indium, yttrium, silver, copper, cobalt, potassium, titanium, zirconium, vanadium, tantalum, cadmium, quicksilver, chromium, molybdenum, tungsten, thallium, gold and lead. More preferably, the promoting metal is selected from indium, copper and silver. More than two metal can be used as the promoting component. The amount of the promoting metal is from 0.001 to 5 preferably 0.001 to 2 parts by weight per one part of ruthenium metal. The association of the promoting component with ruthenium may be carried out in conventional ways such as by dipping, ion-exchanging and coprecipitating. The promoting metal may be associated with ruthenium metal on a carrier either by separately adding it to a supported ruthenium catalyst or by incorporating both ruthenium and the promoting component with a carrier at the same time. Activation under a reducing condition may also be effective to the promoted ruthenium catalyst.

Aromatic hydrocarbons such as benzene, toluene, ethyl benzene and xylenes may be partially hydrogenated to a corresponding cyclic olefin according to the present invention. In carrying out the partial hydrogenation process of the present invention, the hydrogen-containing gas is passed into the aqueous dispersion containing an aromatic hydrocarbon, water, phosphorus acid salt and ruthenium catalyst until sufficient hydrogen is absorbed. The process can be carried out either batchwise or continuously. If desired, the aromatic hydrocarbon can be diluted with a suitable diluent such as a saturated hydrocarbon. The amount of water is 0.01 to 10 parts by weight per one part of the aromatic hydrocarbon. The reaction temperature is in the range of from 0° to 300° C., preferably from 50° to 200° C. The pressure of hydrogen is 1 to 300 kg/cm$^2$ preferably 50 to 200 kg/cm$^2$. The process of the present invention can be carried out in a conventional pressure reactor suitable for hydrogenation under the reaction conditions. Vigorous agitation is preferred because of vigorous and intimate contact of the two liquid phases, i.e. water and aromatic hydrocarbon, with hydrogen.

After the hydrogenation reaction is terminated, the desired olefin can be separated from the reaction mixture by any conventional method such as fractional distillation, extraction and the like. The recovered aromatic hydrocarbon can be recycled to the reaction zone. The aqueous phase containing the catalyst and other additives can also be recycled to the reaction zone.

The following examples demonstrate without limiting the present invention. The terms conversion, yield and selectivity used in the examples are defined as follows.

$$\text{conversion (\%)} = 1 - \frac{\text{weight of unconverted aromatic hydrocarbon remaining in products mixture}}{\text{total weight of products}} \times 100$$

$$\text{yield (\%)} = \frac{\text{weight of cycloolefin contained by products}}{\text{total weight of products}} \times 100$$

$$\text{selectivity (\%)} = \frac{\text{yield}}{\text{conversion}} \times 100$$

EXAMPLE 1

Benzene was converted to cyclohexene over a ruthenium catalyst promoted with copper and potassium in an aqueous dispersion containing cobalt orthophosphate as a reaction modifier.

The catalyst had been prepared by the following procedure. 4.48 g of the ammonium exchanged form of natural mordenite (occurrence in Fukushima prefec.) powder was impregnated with an aqueous solution containing 0.85 g of Cu(NO$_3$)$_2$.3H$_2$O and 0.58 g of KNO$_3$ at 90°–100° C. The residual solid was washed several times with water by decantation and then immersed in an aqueous solution containing 0.50 g of RuCl$_3$ H$_2$O followed by evaporation. The dried solid was crushed to a powder and treated with hydrogen at 200° C. for 2 hours.

The catalyst contained 3.7 weight % ruthenium 1.0 weight % copper and 0.9 weight % potassium.

In a stainless (SUS 27) 500 ml stirred autoclave, were placed 30 ml of benzene and 30 ml of water together with 0.5 g of catalyst and 5.0 g of cobalt orthophosphate Co$_3$(PO$_4$)$_2$.8H$_2$O. Hydrogen was charged to the reactor in an amount sufficient to provide a pressure of 40 kg/cm$^2$, and the contents of the reactor were stirred for 50 minutes at about 170° C.

The organic phase of the reaction mixture was analyzed by gas chromatography for cyclohexane, cyclohexene and benzene, and the conversion, selectivity and yield were calculated.

The results showed a total conversion of 51.1% of benzene with a selectivity to cyclohexene of 47.9%. The yield of cyclohexene was, thus, 24.5% based on the initially charged benzene.

In the absence of any reaction modifier such as cobalt orthophosphate, a comparison run was carried out in a manner similar to that of the preceding example except that the reaction time was 11 minutes.

Analysis of the reaction mixture showed a total conversion of 46.8% of benzene with a selectivity to cyclohexene of 27.5%. The yield of cyclohexene was, thus, only 12.9% based on the initially charged benzene. Comparing the invention run to the comparison run shows that the invention run exhibited an improved selectivity to cyclohexene, and thus, a higher yield of cyclohexene.

EXAMPLE 2

Toluene was converted to methylcyclohexenes over a ruthenium catalyst promoted with copper and silver in an aqueous dispersion containing cobalt orthophosphate.

The catalyst had been prepared in a manner similar to that of Example 1 by drying an aqueous slurry of 4.48 g of the powdered ammonium form of natural mordenite (occurrence in Fukushima prefec.) and of Cu(NO$_3$)$_2$.3H$_2$O, 0.35 g of AgNO$_3$ and 0.50 g of RuCl$_2$.H$_2$O. The dried solid was crushed to a powder and treated with hydrogen at 200° C. for 2 hours.

0.5 g of the powdered catalyst containing 3.1 weight % ruthenium, 1.2 weight % copper and 3.4 weight % of silver, and 5.0 g of Co$_3$(PO$_4$)$_2$.8H$_2$O was charged into the same autoclave as that of Example 1 together with 30 ml of toluene and 30 ml of water. The reactor was pressurized with hydrogen at 40 kg/cm$^2$ and the contents of the reactor were stirred for 100 minutes at 170° C.

The results showed a total conversion of 45.8% of toluene to the hydrogenated products with a selectivity to methylcyclohexenes of 48.6%. Methycyclohexenes containing about 55% of 1-methylcyclohexene and the remainder consisting of a mixture of 3-methylcyclohexene and 4-methylcyclohexene, were obtained in 22.2% yield.

The results of a comparison run in which toluene was converted to methylcyclohexenes in the absence of any reaction modifier using the same reactor and catalyst as those of the invention run described above showed a total conversion of 43.5% with a selectivity to methylcyclohexenes of 23.1%. The yield of methylcyclohexenes were, therefore, only 10.0% (7.3% of 1-methylcyclohexene and 2.7% of 3- and 4-methylclohexenes).

EXAMPLE 3

In this example, p-xylene was converted to dimethylcyclohexenes over a ruthenium catalyst promoted with cobalt and silver in an aqueous dispersion containing cobalt orthophosphate.

The catalyst had been prepared in a manner similar to that of Example 1 by drying an aqueous slurry of 4.48 g of the powdered ammonium form of natural mordenite (occurrence in Fukushima prefec.) and 1.11 g of Co($NO_3$)$_2$.6H$_2$O, 0.35 g of AgNO$_3$ and 0.50 g of RuCl$_3$.H$_2$O.

Into the same autoclave as that of Example 1, 0.5 g of the powdered catalyst containing 4.4 weight % ruthenium, 2.1 weight % cobalt and 3.7 weight % silver was charged together with 30 ml of p-xylene, and 30 ml of an aqueous dispersion containing 1.5 g of Co$_3$(PO$_4$)$_2$.8H$_2$O. The reactor was pressurized to 40 kg/cm$^2$ and then stirred for 150 minutes at 170° C.

The results showed a total conversion of 55.0% and a selectivity to dimethylcyclohexenes of 59.8%. Dimethycyclohexenes consisting of a mixture of two isomers were obtained in 32.9% yield. About 47.6% of the mixture was 1.4 dimethyl cyclohexenes.

In the absence of any reaction modifier, using a reactor and catalyst scheme as used in the above run the hydrogenation of p-xylene was attempted at a pressure of 40 kg/cm$^2$, and a temperature of 170° C. for 28 minutes.

The results of this comparison run showed a selectivity to dimethylcyclohexenes of 23.9% at a conversion of p-xylene of 48.7%. The yield of dimethylcyclohexenes was, therefore, 11.6%.

EXAMPLE 4

A series of runs were carried out in which benzene was selectively hydrogenated to cyclohexene in an aqueous dispersion containing various metal salts of phosphorus acids using a commercially available 5% Ru/Alumina powder (Japan Engerhard Co., 100 mesh pass).

The runs were carried out in a stainless (SUS 32) 30 ml reactor. Unless otherwise noted, each run employed 0.3 g of catalyst, 0.2 g of a metal salt of a phosphorus acid, 3 g of water, and 3 g of benzene. The reactor was flushed with hydrogen, then pressured to 10 kg/cm$^2$ with hydrogen.

The reactor was immersed in a water bath kept constant at 70° C., then shaked for 4 hours. The pressure of hydrogen was kept constant at 10 kg/cm$^2$ throughout the operation.

The results of these tests are shown in Table 1 and Table 2.

In a manner similar to that of the preceding examples, comparison runs were carried out in the absence of any salt of a phosphorus acid.

The results of comparison runs are shown in Table 3. The conversion of benzene, the selectivity to cyclohexene and the yield of cyclohexene at different reaction times were calculated.

Comparing invention runs (the data in Table 1 and Table 2) which were carried out in the presence of various salts of phosphorus acids comparison runs (the data in Table 3), it is shown that the invention runs exhibited a greater selectivity to cyclohexene at relatively high conversion based on the same degree of conversion of benzene as that of the comparison runs. The data in Table 1 and Table 2 also shows that the process is operable with several different salts of phosphorus acids containing a metal selected from Group II, III, IV, V, VI, VII and VIII metals of the periodic table. Salts of cobalt, nickel and copper are shown to be more suitable modifiers for the invention process.

TABLE 1

| Run | Modifier | *BZ Conversion (%) | **HK Selectivity (%) | **HX Yield (%) |
|---|---|---|---|---|
| 1 | Mg$_3$(PO$_4$)$_2$ . 8H$_2$O | 29.9 | 7.0 | 2.1 |
| 2 | Mg$_2$P$_2$O$_7$.XH$_2$O | 31.6 | 1.7 | 0.5 |
| 3 | MgHPO$_4$.3H$_2$O | 23.0 | 7.8 | 1.8 |
| 4 | CaHPO$_4$.2H$_2$O | 25.8 | 5.4 | 1.4 |
| 5 | Cr$_2$P$_4$O$_7$ | 32.1 | 4.3 | 1.4 |
| 6 | Ba(PO$_3$)$_2$ | 34.1 | 2.3 | 0.8 |
| 7 | BaHPO$_4$ | 37.7 | 3.3 | 1.3 |
| 8 | Ba$_2$P$_2$O$_7$.2H$_2$O | 28.8 | 6.5 | 1.9 |
| 9 | CrPO$_4$ 2H$_2$O | 38.3 | 2.4 | 0.9 |
| 10 | Mn$_3$(PO$_4$)$_2$ | 38.8 | 4.0 | 1.6 |
| 11 | MnHPO$_4$.3H$_2$O | 20.7 | 7.5 | 1.6 |
| 12 | Mn$_2$P$_2$O$_7$ | 26.6 | 3.2 | 0.8 |
| 13 | MnNH$_4$PO$_4$ | 20.8 | 3.3 | 0.7 |
| 14 | Co$_3$(PO$_4$)$_2$ . 8H$_2$O | 26.1 | 15.8 | 4.1 |
| 15 | Ni$_3$(PO$_4$)$_2$ | 18.1 | 11.2 | 2.0 |
| 16 | Ni$_2$P$_2$O$_7$ | 17.7 | 7.6 | 1.3 |
| 17 | Cu$_2$P$_2$O$_7$ 3H$_2$O | 31.7 | 9.3 | 3.0 |
| 18 | Ch$_3$(PO$_4$)$_2$ . 3H$_2$O | 9.0 | 16.2 | 1.5 |
| 19 | Zn$_3$(PO$_4$)$_2$.4H$_2$O | 23.8 | 3.9 | 0.9 |
| 20 | Zn$_2$P$_2$O$_2$ | 15.0 | 6.6 | 1.0 |
| 21 | ALPO$_4$ | 35.3 | 6.0 | 2.1 |
| 22 | Sn$_2$P$_2$O$_7$ | 21.6 | 1.9 | 0.4 |
| 23 | CoHPO$_4$.xH$_2$O | 22.6 | 9.2 | 2.1 |
| 24 | Co$_2$P$_2$O$_2$.xH$_2$O | 14.2 | 11.3 | 5.0 |
| 25 | FePO$_2$.4H$_2$O | 25.2 | 2.3 | 0.6 |
| 26 | Co$_2$P$_2$O$_7$ | 24.2 | 7.0 | 1.7 |

*BZ:Benzene.
**HX:Hexene

TABLE 2

| Run | Modifier (g) | Time (hr) | BZ Conver (%) | HX Selectivity (%) | HX Yield (%) |
|---|---|---|---|---|---|
| 1 | Co$_3$(PO$_4$)$_2$ . 8H$_2$O (0.2) | 2 | 9.6 | 21.5 | 2.1 |
| 2 | CO$_3$(PO$_4$)$_2$ . 8H$_2$O (0.2) | 4 | 20.4 | 16.1 | 3.6 |
| 3 | CO$_3$(PO$_4$)$_2$ . 8H$_2$O (0.2) | 6 | 20.9 | 13.6 | 2.8 |
| 4 | CO$_3$(PO$_4$)$_2$ . 8H$_2$O (0.2) | 2 | 28.2 | 12.0 | 3.4 |
| 5 | CO$_3$(PO$_4$)$_2$ . 8H$_2$O (0.1) | 2 | 14.3 | 28.6 | 4.1 |
| 6 | CO$_3$(PO$_4$)$_2$ . 8H$_2$O (0.1) | 4 | 17.0 | 21.2 | 3.8 |
| 7 | CO$_3$(PO$_4$)$_2$ . 8H$_2$O (0.1) | 6 | 20.2 | 18.7 | 3.8 |
| 8 | CO$_3$(PO$_4$)$_2$ . 8H$_2$O (0.3) | 2 | 14.9 | 27.6 | 4.1 |
| 9 | CO$_3$(PO$_4$)$_2$ . 8H$_2$O (0.3) | 4 | 22.9 | 17.1 | 3.9 |
| 10 | CO$_3$(PO$_4$)$_2$ . 8H$_2$O (0.3) | 6 | 23.6 | 14.9 | 3.5 |
| 11 | CO$_2$P$_2$O$_7$ (0.2) | 2 | 15.3 | 23.5 | 3.6 |
| 12 | CO$_2$P$_2$O$_7$ (0.2) | 6 | 41.1 | 8.9 | 3.7 |
| 13 | Ni$_3$(PO$_4$)$_2$ 7H$_2$O (0.1) | 2 | 16.2 | 22.8 | 3.7 |
| 14 | Ni$_3$(PO$_4$)$_2$ . 7H$_2$O (0.1) | 4 | 31.9 | 13.6 | 4.8 |
| 15 | Ni$_3$(PO$_4$)$_2$ . 7H$_2$O (0.1) | 6 | 52.3 | 10.3 | 5.4 |
| 16 | Ni$_3$(PO$_4$)$_2$ . 7H$_2$O (0.3) | 2 | 6.6 | 23.9 | 1.6 |
| 17 | Ni$_3$(PO$_4$)$_2$ . 7H$_2$O (0.3) | 4 | 31.3 | 12.8 | 4.0 |
| 18 | Ni$_3$(PO$_4$)$_2$ . 7H$_2$O (0.3) | 6 | 44.3 | 10.2 | 4.5 |
| 19 | Cu$_2$P$_2$O$_7$ . 3H$_2$O (0.1) | 2 | 26.2 | 15.9 | 4.2 |
| 20 | Cu$_2$P$_2$O$_7$ . 3H$_2$O (0.1) | 4 | 60.1 | 6.1 | 3.7 |
| 21 | Cu$_2$P$_2$O$_7$ . 3H$_2$O (0.1) | 6 | 92.4 | 2.6 | 2.4 |
| 22 | Cu$_2$P$_2$O$_7$ . 3H$_2$O (0.3) | 2 | 11.4 | 15.1 | 1.7 |
| 23 | Cu$_2$P$_2$O$_7$ . 3H$_2$O (0.3) | 4 | 30.3 | 8.8 | 2.7 |
| 24 | Cu$_2$P$_2$O$_7$ . 3H$_2$O (0.3) | 6 | 18.5 | 6.6 | 2.5 |
| 25 | (a) (0.3) | 2 | 7.1 | 21.2 | 1.5 |
| 26 | (a) (0.3) | 4 | 17.4 | 17.4 | 3.0 |
| 27 | (a) (0.3) | 6 | 28.6 | 15.1 | 4.3 |

(a) a mixture of equal weight of Co$_3$(PO$_4$)$_2$ 8H$_2$O, Ni$_3$(PO$_4$)$_2$ 7H$_2$O and Cu$_2$P$_2$O$_7$ . 3H$_2$O

TABLE 3

| *** Control Run | Time (min) | BZ Conversion (%) | HX Selectivity (%) | HX Yield (%) |
| --- | --- | --- | --- | --- |
| 1 | 4 | 0.6 | 12.1 | 0.08 |
| 2 | 5 | 0.8 | 18.4 | 0.14 |
| 3 | 6 | 1.2 | 11.5 | 0.14 |
| 4 | 8 | 1.7 | 10.4 | 0.18 |
| 5 | 10 | 2.3 | 9.4 | 0.21 |
| 6 | 12 | 3.3 | 5.5 | 0.18 |
| 7 | 15 | 4.0 | 7.8 | 0.32 |
| 8 | 20 | 5.0 | 6.1 | 0.31 |
| 9 | 25 | 5.7 | 4.9 | 0.28 |
| 10 | 30 | 8.3 | 2.8 | 0.23 |
| 11 | 35 | 10.0 | 1.4 | 0.14 |
| 12 | 37 | 12.1 | trace | trace |
| 13 | 40 | 12.9 | 0.6 | 0.08 |
| 14 | 45 | 13.9 | trace | trace |
| 15 | 50 | 12.3 | 0.9 | 0.11 |
| 16 | 55 | 15.3 | 0.8 | 0.12 |
| 17 | 60 | 19.1 | 0.1 | 0.01 |

***Benzene was hydrogenated to cyclohexene and cyclohexene in the absence of any reaction modifier.

EXAMPLE 5

Another series of runs were carried out in which benzene was selectively hydrogenated to cyclohexene by the process of the present invention.

The various catalysts were generally prepared by drying an aqueous slurry of the powdered support and appropriate quantities of $RuCl_3.H_2O$. The dried solids were crushed to a powder and treated with hydrogen at 200° C. for 2 hours.

The runs were carried out using cobalt orthophosphate as a reaction modifier in a manner similar to that of Example 4.

Each runs employed 0.3 g of catalyst containing 5 wt. % ruthenium, 0.1 g of $Co_3(PO_4)_2.8H_2O$, 3 g of water and 3 g of benzene.

Comparison runs also carried out using a same reactor and catalyst as those of the invention runs in the absence of any reaction modifier. In comparison runs, a reaction time was controlled to keep the about same degree of a conversion of benzene as that of the corresponding invention run.

The results of these runs are shown in Table 4.

Comparing invention runs to comparison runs shows that the invention runs exhibited a greater selectivity to cyclohexene and, thus, a greater yield of cyclohexene.

The data in Table 4 also show that the invention process is operable with a ruthenium catalyst supported on several solid material.

Table 4

| | | Invention run[a] | | | | Comparison run[b] | | | |
| --- | --- | --- | --- | --- | --- | --- | --- | --- | --- |
| Run | Catalyst carrier | Time (hr) | BZ conversion (%) | HX selectivity (%) | HX yield (%) | Time (hr) | BZ conversion (%) | HX selectivity (%) | HX yield (%) |
| 1 | γ-Alumina | 2 | 15.2 | 15.7 | 2.4 | 2 | 13.1 | 2.5 | 0.3 |
| 2 | Silica | 2 | 9.4 | 25.0 | 2.4 | 1 | 9.4 | 13.0 | 1.2 |
| 3 | Natural mordenite[c] | 4 | 15.7 | 16.8 | 2.6 | 1 | 16.9 | 3.3 | 0.6 |
| 4 | Molecularsieve 13X[d] | 4 | 19.7 | 26.5 | 5.2 | 1 | 14.0 | 1.2 | 0.2 |
| 5 | Molecularsieve 10X[d] | 2 | 13.7 | 11.8 | 1.6 | 1 | 19.2 | 1.9 | 0.4 |
| 6 | Neobeads-p[e] | 2 | 13.7 | 11.8 | 1.6 | 1 | 10.8 | 4.6 | 0.5 |
| 7 | Silibeads[e] | 2 | 11.8 | 9.5 | 1.1 | 0.5 | 18.6 | 5.0 | 0.9 |
| 8 | Diatomaceous earth | 4 | 16.5 | 15.5 | 2.6 | 1 | 17.1 | 1.0 | 0.2 |
| 9 | Molecularsieve 4A[d] | 2 | 14.9 | 27.5 | 4.1 | 1 | 11.9 | 12.3 | 1.5 |
| 10 | Mordenite JM-3[f] | 4 | 12.4 | 14.4 | 1.8 | 0.5 | 39.0 | 1.4 | 0.5 |
| 11 | Activated clay | 4 | 21.9 | 3.7 | 0.8 | 1 | 15.5 | 1.9 | 0.3 |
| 12 | Natural mordenite[g] | 4 | 19.5 | 21.7 | 4.3 | 1 | 19.0 | 4.5 | 0.9 |
| 13 | MgO | 4 | 45.7 | 1.3 | 0.6 | 1 | 56.5 | 0.02 | 0.01 |
| 14 | Cobalt powder | 4 | 3.4 | 35.5 | 1.2 | 1 | 3.6 | 23.0 | 0.8 |
| 15 | Copper powder | 4 | 1.0 | 47.5 | 0.5 | 0.5 | 1.8 | 14.9 | 0.3 |
| 16 | Molecular sieve 3A[d] | 4 | 30.3 | 17.5 | 5.3 | 2 | 68.1 | 0.2 | 0.2 |
| 17 | Molecular sieve 5A[d] | 4 | 21.2 | 22.6 | 4.8 | 0.5 | 17.8 | 2.4 | 0.4 |
| 18 | Kaolin | 4 | 18.1 | 6.0 | 1.1 | 0.5 | 16.2 | 3.0 | 0.5 |

[a]Cobalt orthophosphate was used as a reaction modifier.
[b]Hydrogenation was carried in the absence of any reaction modifier.
[c]Natural zeolite occuring in Fukushima prefec.
[d]Synthetic geolite of UCC (linde).
[e]Commercial high purity form of silica-alumina.
[f]Synthetic zeolite of Japan Chemical Ind. Ltd.
[g]Natural zeolite occurring in Miyagi prefec.

EXAMPLE 6

A series of runs were carried out in which benzene was converted to cyclohexene by the process of the present invention. In these runs, the various promoted ruthenium catalysts were used toghther with an aqueous dispersion containing cobalt orthophosphate as a reaction modifier.

The runs were carried out in a manner similar to that of Example 1. The catalyst, cobalt orthophosphate, water and benzene were charged into the stainless (SUS 27) 500 ml stirred autoclave. Each runs employed 0.5 g of catalyst, 5.0 g of $Co_3(PO_4)_2.H_2O$, 30 ml of water and 30 ml of benzene. The reactor was flushed with hydrogen and vented several times, and then, pressured again with hydrogen to 40 kg/cm$^2$, and the contents of the reactor were stirred at about 170° C.

The various catalyst had been prepared as described in Example 1 by drying an aqueous slurry of the powdered support containing reaction promoting metals, and apporpriate amounts of $RuCl_2.H_2O$. The powdered catalysts were treated with hydrogen at 200° C. for 2 hours.

To demonstrate the advantage of the present process, comparison runs were also carried out using a same reactor and catalyst as that of the invention runs in the absence of any reaction modifier, such as cobalt orthophosphate. These results are shown in Table 5.

The invention runs of Table 5 show that benzene was converted to cyclohexene at high selectivities with relatively high conversion.

Invention runs which employed an aqueous dispersion containing a salt of phosphorus acid as a reaction modifier, namely, cobalt orthophosphate show advantage in improving a selectivety to cyclohexene over the comparison runs carried out in the absence of any reaction modifier, and thus, cyclohexene is obtained in a greater yield.

The data in the table also show that the invention process is successfully operable with several different catalyst promoted with metals such as potassium, copper, silver, gold, cadmium, quicksilver, indium, thallium, yttrium, titanium, zirconium, lead, vanadium, tantalum, chromium, molybdenum, tungsten, iron, nickel and cobalt.

modifier. Into a stainless (SUS 27) 500 ml autoclave, 0.5 g of catalyst and 30 ml of benzene were charged together with appropriate amounts of water and $Co_3(PO_4)_2.8H_2O$. The reactor was pressurized with hydrogen and stirred at 150° C.

The results of these tests are shown in Table 6. Comparing invention runs to comparison runs 19 and 20 shows that the invention runs exhibited a greater selectivity to cyclohexene. In the absence of water and cobalt orthophosphate, the attempted hydrogenation of benzene using the ruthenium catalyst system resulted in a largely uncontrollable reaction, which produced insignificant amounts of cyclohexene, if any, as shown in the comparison run 19 of Table 6.

Table 5

| | | Invention run | | | Comparison run | | |
|---|---|---|---|---|---|---|---|
| Run | Catalyst | Time (min) | BZ conversion (%) | HX selectivity (%) | HX yield (%) | Time (min) | BZ conversion (%) | HX selectivity (%) | HX yield (%) |
| 1 | 4.4%Ru-2.1%Co-3.7%Ag/AM | 25 | 49.8 | 41.2 | 20.5 | 11 | 52.1 | 9.3 | 4.8 |
| 2 | 3.2%Ru-5.5%K/AM | 37 | 51.4 | 39.5 | 20.3 | 16 | 49.7 | 10.1 | 5.0 |
| 3 | 3.5%Ru-0.4%Co-3.2%K/AM | 29 | 50.6 | 41.2 | 20.9 | 15 | 51.0 | 8.8 | 4.5 |
| 4 | 3.4%Ru-1.2%Cu/M | 35 | 51.9 | 40.9 | 21.2 | 10 | 49.8 | 15.2 | 7.6 |
| 5 | 3.1%Ru-1.2%Cu-3.4%Ag/AM | 37 | 51.8 | 47.4 | 24.5 | 12 | 53.0 | 18.2 | 9.6 |
| 6 | 3.8%Ru-1.2%Cu-0.9%Co/AM | 38 | 50.8 | 44.6 | 22.7 | 11 | 50.3 | 18.0 | 9.1 |
| 7 | 5.0%Ru-1.0%Cu-1.0%Co/M | 45 | 51.6 | 40.2 | 20.2 | 13 | 48.4 | 16.5 | 8.0 |
| 8 | .0%Ru-1.0%Cu/SiO$_2$ | 33 | 51.1 | 40.5 | 20.7 | 22 | 54.1 | 21.0 | 11.3 |
| 9 | 5.0%Ru-1.0%Cu/AM | 75 | 51.8 | 45.7 | 23.6 | 12 | 50.1 | 17.2 | 8.6 |
| 10 | 5.0%Ru-1.0%Y/AM | 47 | 51.2 | 40.3 | 20.6 | 9 | 56.1 | 7.1 | 4.0 |
| 11 | 5.0%Ru-0.5%In/AM | 90 | 48.9 | 40.3 | 19.7 | 31 | 45.8 | 18.1 | 8.3 |
| 12 | 5.0%Ru-0.5%Hg/AM | 35 | 48.3 | 44.3 | 21.4 | 13 | 50.3 | 10.0 | 5.0 |
| 13 | 5.0%Ru-0.5%Cd/AM | 90 | 47.9 | 43.7 | 20.3 | 21 | 49.2 | 28.1 | 13.9 |
| 14 | 5.0%Ru-1.0%Au/AM | 33 | 49.5 | 43.4 | 21.5 | 10 | 55.3 | 4.5 | 2.5 |
| 15 | 5.0%Ru-2.0%Ag/AM | 37 | 49.7 | 43.0 | 21.4 | 10 | 51.5 | 6.3 | 3.2 |
| 16 | 5.0%Ru-2.0%Ti/AM | 64 | 49.0 | 19.2 | 9.4 | 11 | 54.5 | 8.0 | 4.4 |
| 17 | 5.0%Ru-1.0%Zr/AM[a] | 30 | 50.7 | 27.5 | 13.9 | 10 | 54.4 | 5.9 | 3.2 |
| 18 | 5.0%Ru-1.0%Pb/AM | 65 | 43.6 | 21.2 | 9.3 | 11 | 50.0 | 1.2 | 0.6 |
| 19 | 5.0%Ru-2.0V/AM | 46 | 48.0 | 37.0 | 17.7 | 17 | 51.9 | 11.0 | 5.7 |
| 20 | 5.0%Ru-1.0%Ta/AM[a] | 27 | 48.8 | 30.5 | 14.9 | 10 | 55.9 | 5.3 | 3.0 |
| 21 | 5.0%Ru-1.0%Cr/AM | 32 | 48.3 | 32.4 | 15.6 | 10 | 54.5 | 6.4 | 3.5 |
| 22 | 5.0%Ru-0.2%Mo/AM[a] | 35 | 50.2 | 33.3 | 16.7 | 12 | 55.4 | 7.8 | 4.3 |
| 23 | 5.0%Ru-1.0%W/AM[b] | 56 | 46.6 | 25.9 | 12.1 | 26 | 47.6 | 7.1 | 3.4 |
| 24 | 5.0%Ru-0.5%Tl/AM | 58 | 45.2 | 39.1 | 17.6 | 9 | 51.5 | 1.9 | 1.0 |
| 25[c] | 5.0%Ru-1.0%Fe/SA | 52 | 48.1 | 23.5 | 11.3 | 30 | 49.5 | 20.0 | 9.9 |
| 26 | 5.0%Ru-1.0%Ni/SA | 32 | 46.1 | 29.4 | 13.6 | 13 | 50.8 | 8.3 | 4.2 |
| 27 | 5.0%Ru-1.0%Co/SA | 38 | 50.9 | 31.4 | 16.0 | 19 | 48.2 | 11.6 | 5.6 |

AM:Ammonium ion exchanged form of natural mordenite (occuring in Fukushima prefec.)
M:Natural mordenite (occiring in Fukushima prefec.)
SA:Synthetic zeolite "Molecularsieve 3A" of UCC (Linde)
(a):The Catalysts were prepared from an ethanolic slurry of the powdered support and the halide salts of the desired metals.(b):The catalyst was prepared by immersing the powdered support in a diethyl ether solution containing $WCl_6$.
(c):2 g of $Co_3(PO_4)_2 \cdot 8H_2O$ used.

EXAMPLE 7

Benzene was converted to cyclohexene under the various reaction conditions by the process of the present invention.

Each run carried out in a manner similar to that of Example 1 using a commercially available 5% ruthenium/alumina catalyst powder (Japan Engerhard Co., 100 mesh pass) and cobalt orthophosphate as a reaction The comparison run 20 which was carried out in the absence of water shows no advantage over the invention runs, and thus, demonstrates that the presence of sufficient water to form an aqueous dispersion containing a salt of phosphorus acid is important to operate the process of the present invention.

The data in Table 6 also show that the invention is operable in the wide ranges of various reaction variables.

Table 6

| | Reaction variables | | | | Results of hydrogenation of benzene | | |
|---|---|---|---|---|---|---|---|
| Run | Benzene (ml) | Water (ml) | $Co_3(PO_4)_2 \cdot 8H_2O$ (g) | Hydrogen pressure (kg/cm$^2$) | Time (min) | BZ coversion (%) | HX selectivity (%) | HX yield (%) |
| 1 | 30 | 10 | 4.5 | 40 | 55 | 43.8 | 14.9 | 6.5 |
| 2 | 30 | 20 | 9.0 | 40 | 55 | 40.9 | 18.3 | 7.5 |
| 3 | 30 | 10 | 9.0 | 40 | 80 | 40.8 | 16.8 | 6.9 |
| 4 | 30 | 10 | 13.5 | 40 | 160 | 38.0 | 14.6 | 5.6 |
| 5 | 30 | 30 | 13.5 | 40 | 45 | 42.5 | 18.9 | 8.0 |
| 6 | 30 | 40 | 18.0 | 40 | 60 | 42.0 | 19.2 | 8.0 |
| 7 | 30 | 90 | 4.6 | 40 | 25 | 45.0 | 16.6 | 7.5 |

Table 6-continued

| | Reaction variables | | | | Results of hydrogenation of benzene | | | |
|---|---|---|---|---|---|---|---|---|
| Run | Benzene (ml) | Water (ml) | Co$_3$(PO$_4$)$_2$ · 8H$_2$O (g) | Hydrogen pressure (kg/cm$^2$) | Time (min) | BZ coversion (%) | HX selectivity (%) | HX yield (%) |
| 8 | 30 | 60 | 4.5 | 40 | 23 | 41.1 | 19.5 | 8.0 |
| 9 | 30 | 30 | 4.5 | 40 | 30 | 41.1 | 19.0 | 7.8 |
| 10 | 30 | 30 | 4.6 | 110 | 9 | 49.4 | 19.4 | 9.6 |
| 11 | 30 | 30 | 4.6 | 135 | 8 | 48.7 | 17.5 | 8.5 |
| 12 | 30 | 30 | 4.5 | 10 | 450 | 47.0 | 8.2 | 3.8 |
| 13 | 30 | 30 | 4.5 | 110 | 14 | 66.1 | 19.6 | 13.8 |
| 14 | 30 | 30 | 4.5 | 110 | 18 | 77.9 | 16.8 | 13.1 |
| 15 | 30 | 30 | 4.5 | 110 | 5 | 29.2 | 20.0 | 5.9 |
| 16 | 30 | 30 | 4.5 | 110 | 3 | 21.2 | 21.3 | 4.5 |
| 17 | 30 | 30 | 4.5 | 110 | 1 | 6.6 | 12.3 | 0.8 |
| 18 | 30 | 30 | 4.5 | 110 | 20 | 85.1 | 13.2 | 11.2 |
| 19[a] | 30 | 0 | 0 | 40 | 2 | 69.2 | trace | trace |
| 20[a] | 30 | 0 | 4.5 | 40 | 2 | 68.5 | 1.3 | 0.9 |

[a]Comparison run

What we claim is:

1. A process for the conversion of aromatic hydrocarbons to the corresponding cyclic olefins which comprises partially hydrogenating an aromatic ring contained within said aromatic hydrocarbon with hydrogen and a ruthenium catalyst at a temperature of 0° to 300° C. under a pressure of 1 to 300 kg/cm$^2$ in an aqueous dispersion containing a metal salt of a phosphorus acid, wherein said metal is a member selected from the group consisting of Group II to Group VIII metals and wherein said ruthenium catalyst is supported on a solid carrier.

2. A process according to claim 1 wherein said aromatic hydrocarbon is selected from the group consisting of benzene, and toluene.

3. A process according to claim 1 wherein said aromatic hydrocarbon is benzene and the corresponding cyclic olefin is cyclohexene.

4. A process according to claim 1 wherein said ruthenium catalyst comprises ruthenium metal promoted with at least one metal selected from the group consisting of indium, yttrium, silver, copper, cobalt, potassium, titanium, zirconium, vanadium, tantalum, cadmium, quicksilver, chromium, molybdenum, tungsten, thallium, gold and lead.

5. A process according to claim 1 wherein said ruthenium catalyst is supported by a carrier.

6. A process according to claim 5 wherein said carrier comprises silica-alumina.

7. A process according to claim 5 wherein said carrier comprises zeolite.

8. A process according to claim 1 wherein said ruthenium catalyst is promoted by copper.

9. A process according to claim 1 wherein said ruthenium catalyst is promoted by silver.

10. A process according to claim 1 wherein said ruthenium catalyst is promoted by indium.

11. A process according to claim 1 wherein said metal salt of a phosphorus acid comprises at least one member selected from the group consisting of orthophosphate, metaphosphate, pyrophosphate, polyphosphate, hypophosphate, phosphite and hypophosphite.

12. A process according to claim 1 wherein said metal salt of a phosphorus acid comprises nickel.

13. A process according to claim 1 wherein said metal salt of a phosphorus acid comprises copper.

14. A process according to claim 1 wherein said metal salt of a phosphorus acid comprises cobalt.

15. A process according to claim 1 wherein the amount of said metal salt of a phosphorus acid is about 0.5 to 2000 parts by weight per one part of said ruthenium metal contained in the catalyst.

16. A process according to claim 5 wherein the amount of said ruthenium metal is 0.001 to 25% by weight on the basis of said carrier.

17. A process according to claim 5 wherein the amount of said metal salt of a phosphorus acid is 0.01 to 100 parts by weight per one part of the catalyst, inclusive of said carrier.

18. A process according to claim 4 wherein the amount of said promoting metal is 0.001 to 5 parts by weight per one part of said ruthenium metal.

19. A process according to claim 1 wherein the amount of said water in said aqueous dispersion is 0.01 to 10 parts by weight per one part of said aromatic hydrocarbon.

20. A process as recited in claim 1 wherein said metal salt of a phosphorus acid comprises phosphorus in the pentavalent state.

21. A process as recited in claim 1 wherein said metal salt of a phosphorus acid comprises phosphorus in the trivalent state.

* * * * *

UNITED STATES PATENT AND TRADEMARK OFFICE
CERTIFICATE OF CORRECTION

PATENT NO. : 4,197,415
DATED : April 8, 1980
INVENTOR(S) : Hideyuki Aizawa et al It is certified that error appears in the above-identified patent and that said Letters Patent are hereby corrected as shown below:

Col. 1, line 6, after "continuation", --of application Serial No. 837,311-- should have been added.

Col. 2, line 48, "sili" should read --silica--.

Col. 4, line 45, after "and", --0.85 g-- should have been added.

Col. 5, line 26, "47.6%" should read --97.6%--.

Col. 6, Table 1, Run 5, under the column "Modifier", "$Cr_2P_4O_7$" should read --$Sr_2P_2O_7$--.

Col. 6, Table 1, Run 8, under the column "BZ Conversion (%), "28.8" should read --28.2--.

Col. 6, Table 1, Run 18, under the column "Modifier", "$Ch_3(PO_4)_2 \cdot 3H_2O$" should read --$Cu_3(PO_4)_2 \cdot 3H_2O$--.

Col. 6, Table 1, Run 20, under the column "Modifier", "$Zn_2P_2O_2$" should read --$Zn_2P_2O_7$--.

UNITED STATES PATENT AND TRADEMARK OFFICE
CERTIFICATE OF CORRECTION

PATENT NO. : 4,197,415
DATED : April 8, 1980
INVENTOR(S) : Hideyuki Aizawa et al It is certified that error appears in the above-identified patent and that said Letters Patent are hereby corrected as shown below:

Col. 6, Table 1, Run 21, under the column "Modifier", "ALPO$_4$" should read --AlPO$_4$--.

Col. 6, Table 1, Run 24, under the column "Modifier", "Co$_2$P$_2$O$_2$·xH$_2$O" should read --Co$_2$P$_2$O$_7$·xH$_2$O--.

Col. 6, Table 1, Run 24, under the column "BZ Conversion (%)", "14.2" should read --44.2--.

Col. 6, Table 2, the heading for the fourth column "BZ Conver (%)" should read --BZ Conversion (%)--.

Col. 6, Table 2, Run 2, under the column "BZ Conversion (%)", "20.4" should read --22.4--.

Col. 6, Table 2, Run 3, under the column "BZ Conversion (%), "20.9" should read --20.2--.

Col. 6, Table 2, Run 4, under the column "Time (hr)", "2" should read --8--.

Col. 6, Table 2, line 6, under the column "BZ Conversion (%)", "17.0" should read --17.9--.

UNITED STATES PATENT AND TRADEMARK OFFICE
CERTIFICATE OF CORRECTION

PATENT NO. : 4,197,415
DATED : April 8, 1980
INVENTOR(S) : Hideyuki Aizawa et al It is certified that error appears in the above-identified patent and that said Letters Patent are hereby corrected as shown below:

Col. 6, Table 2, Run 13, under the column "Modifier (g)",

"$Ni_3(PO_4)_2$ $7H_2O(0.1)$" should read

--$Ni_3(PO_4)_2 \cdot 7H_2O(0.1)$--.

Col. 6, Table 2, Run 14, under the column "BZ Conversion (%)",

"31.9" should read --34.9--.

Col. 6, Table 2, Run 23, under the column "BZ Conversion (%)",

"30.3" should read --30.7--.

Col. 6, Table 2, Run 24, under the column "BZ Conversion (%)",

"18.5" should read --38.5--.

Col. 9, Table 5, Run 8, under the column "Catalyst",

".0%Ru-1.0%Cu/$SiO_2$" should read --5.0%Ru-1.0%Cu/$SiO_2$--.

Col. 9, Table 5, Run 19, under the column "Catalyst",

"5.0%Ru-2.0V/AM" should read --5.0%Ru-0.2%V/AM--.

Col. 9, Table 5, Run 25 [c], under the column "Catalyst",

"5.0%Ru-1.0%Fe/SA" should read --5.0%Ru-0.5%Fe/3A--.

Col. 9, Table 5, Run 26, under the column "Catalyst",

"5.0%Ru-1.0%Ni/SA" should read --5.0%Ru-1.0%Ni/3A--.

UNITED STATES PATENT AND TRADEMARK OFFICE
CERTIFICATE OF CORRECTION

PATENT NO. : 4,197,415
DATED : April 8, 1980
INVENTOR(S) : Hideyuki Aizawa et al It is certified that error appears in the above-identified patent and that said Letters Patent are hereby corrected as shown below:

Col. 9, Table 5, Run 27, under the column "Catalyst",

"5.0%Ru-1.0%Co/SA" should read --5.0Ru-1.0%Co/3A--.

Col. 9, Table 5, line 43, "occuring" should read --occurring--.
Col. 9, Table 5, line 44, "occiring" should read --occurring--.
Col. 9, Table 5, line 45, "SA" should read --3A--.
Col. 10, Table 6, Run 7, under the column "$Co_3(PO_4)_2 \cdot 8H_2O(g)$", "4.6" should read --4.5--.

Col. 11, Table 6, Runs 10 and 11, under the column "$Co_3(PO_4)_2 \cdot 8H_2O(g)$", "4.6" should read --4.5--.

Signed and Sealed this

Second Day of September 1980

[SEAL]

Attest:

SIDNEY A. DIAMOND

Attesting Officer   Commissioner of Patents and Trademarks